US010202415B1

United States Patent
El Dib et al.

(10) Patent No.: US 10,202,415 B1
(45) Date of Patent: *Feb. 12, 2019

(54) METHOD OF SYNTHESIZING OF 3-OXOLUPENAL NANOPARTICLES

(71) Applicant: KING SAUD UNIVERSITY, Riyadh (SA)

(72) Inventors: Rabab Abd El Moneim Khalil El Dib, Riyadh (SA); Shaza Mohamed Adel Al-Massarani, Riyadh (SA); Manal Ahmed Gasmelseed Awad, Riyadh (SA); Ali Ali El-Gamal, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/788,181

(22) Filed: Oct. 19, 2017

(51) Int. Cl.
  *C07C 7/00* (2006.01)
  *C07C 9/15* (2006.01)
  *C07C 45/58* (2006.01)
  *C07J 53/00* (2006.01)

(52) U.S. Cl.
  CPC ............ *C07J 53/002* (2013.01); *C07C 7/005* (2013.01)

(58) Field of Classification Search
  CPC ............ C07C 7/005; C07C 9/15; C07C 45/58
  See application file for complete search history.

(56) References Cited

U.S. PATENT DOCUMENTS

| 7,858,606 B2 | 12/2010 | Hajduch et al. |
| 8,969,394 B2 | 3/2015 | Blouin et al. |
| 2015/0110862 A1 | 4/2015 | Liu et al. |

FOREIGN PATENT DOCUMENTS

RU   2008 143 847 A   5/2010

OTHER PUBLICATIONS

Viable Herbal Solutions, Production Techniques for herbal extracts, 2006, pp. 1-3.*
Abelwahed et al. Advanced Drug Delivery Reviews, 2006, vol. 58, 1688-1713.*
Mambu et al., "Clerodane and labdane diterpenoids from *Nuxia sphaerocephala,*" Phytochemistry, 67, 444-451, Mar. 2006.
Al-Massarani et al., "New Cytotoxic Seco-Type Triterpene and Labdane-Type Diterpenes from *Nuxia oppositifolia,*" Molecules, 389, Mar. 2017.

* cited by examiner

*Primary Examiner* — Samira J Jean-Louis
(74) *Attorney, Agent, or Firm* — Richard C. Litman

(57) ABSTRACT

A method for synthesizing 3-oxolupenal nanoparticles including isolating 3-oxolupenal from a fraction of *Nuxia oppositifolia* plant, reducing the 3-oxolupenal to obtain a powder of 3-oxolupenal, dissolving the powder of 3-oxolupenal in methanol to form a first solution, adding the first solution to boiling water to form a second solution, sonicating the second solution, and freeze-drying after sonication to obtain the synthesized 3-oxolupenal nanoparticles. The synthesized 3-oxolupenal nanoparticles exhibited cytotoxic effects and antimicrobial effects.

4 Claims, 8 Drawing Sheets

METHOD OF SYNTHESIZING OF 3-OXOLUPENAL NANOPARTICLES

BACKGROUND OF THE INVENTION

1. Field of the Invention

The present subject matter relates to a method of synthesizing nanoparticles and related methods of use. More particularly, the present subject matter relates to a method of synthesizing 3-oxolup-20(29)-en-30-al ("3-oxolupenal") nanoparticles from a fraction of *Nuxia oppositifolia*.

2. Description of the Related Art

Nanomaterials, defined as particles with a size of less than about 100 nm, are at the leading edge of nanoscience and nanotechnology. Nanoparticles frequently exhibit completely new or improved properties compared to corresponding bulk materials with 'regular' particle size. The differences in properties can be attributed to the significant variation in size, morphology, and/or size distribution of the particles. In particular, metal nanoparticles typically exhibit distinctive features including catalytic, optical, magnetic and electrical properties.

In recent years, metal nanoparticles have received particular interest in diverse fields of applied science ranging from material science to biotechnology, such as, e.g., electrical, textile, medicine, cosmetics, agriculture and food. Specifically, metal nanoparticles have potential applications in electronics and photonics, catalysis, information storage, chemical sensing and imaging, environmental remediation, drug delivery, and biological labelling.

Thus, a method of synthesizing 3-oxolupenal nanoparticles with many of the aforementioned benefits and differences compared to standard-sized particles of the same compounds is desired.

SUMMARY OF THE INVENTION

The present subject matter provides a method of synthesizing 3-oxolupenal nanoparticles from a fraction of *Nuxia oppositifolia* plant.

In one embodiment, the method for synthesizing 3-oxolupenal nanoparticles includes isolating 3-oxolupenal from a fraction of *Nuxia oppositifolia* plant and providing a powder of 3-oxolupenal, dissolving the powder of 3-oxolupenal in methanol to form a first solution, adding the first solution to boiling water to form a second solution, sonicating the second solution, and freeze-drying the second solution after sonication to obtain synthesized 3-oxolupenal nanoparticles. The synthesized 3-oxolupenal nanoparticles exhibited cytotoxic and antimicrobial activity.

According to another embodiment, the method for synthesizing 3-oxolupenal nanoparticles includes providing a powder of 3-oxolupenal. The powder of 3-oxolupenal is then dissolved in a solvent to form a first solution. The first solution is then, under ultrasonic conditions, added to boiling water to form a second solution. Finally, the second solution is sonicated and freeze dried to produce 3-oxolupenal nanoparticles.

These and other features of the present subject matter will become readily apparent upon further review of the following specification and drawings. It is to be understood that both the foregoing general description and the following detailed description are exemplary and explanatory only and are not restrictive of the invention. Other objects, features and advantages of the present subject matter will become apparent from the following detailed description taken in conjunction with the accompanying drawings.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION OF THE PREFERRED EMBODIMENTS

Figure 1:
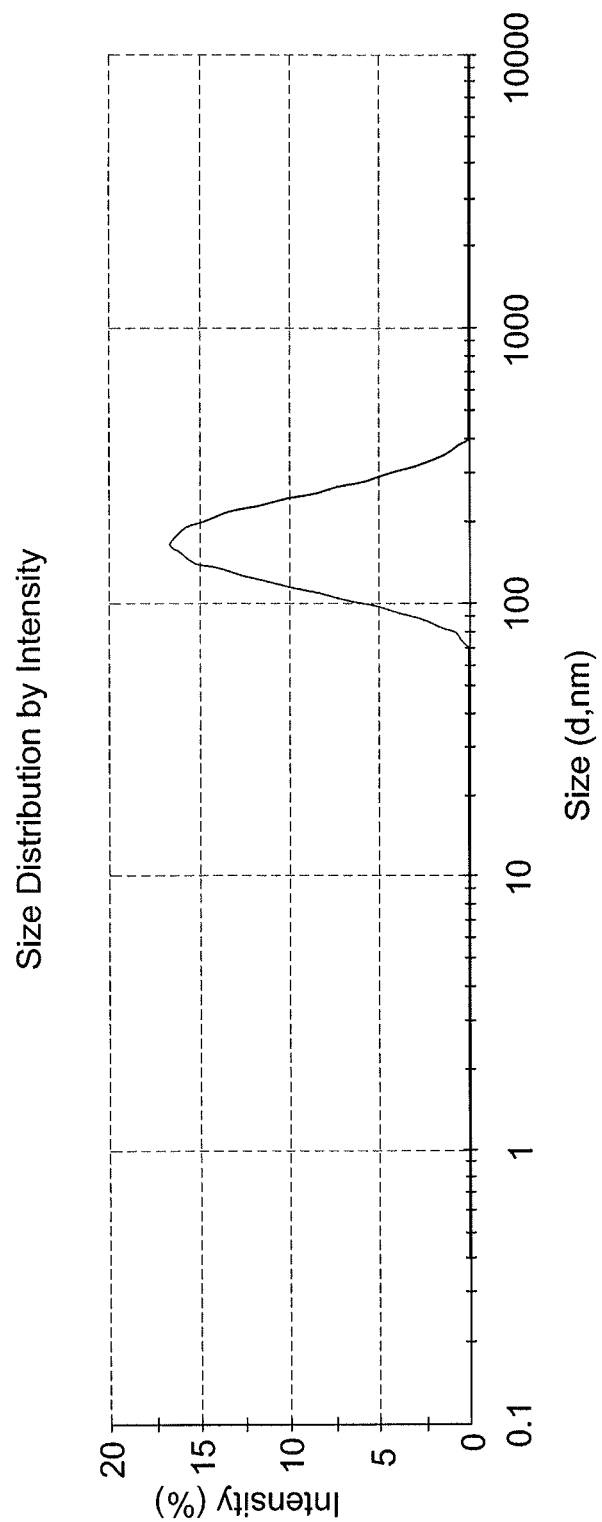
FIG. 1 shows a graph of the average particle size distribution of the 3-oxolupenal nanoparticles in solid state synthesized according to an embodiment.
Figure 2A:
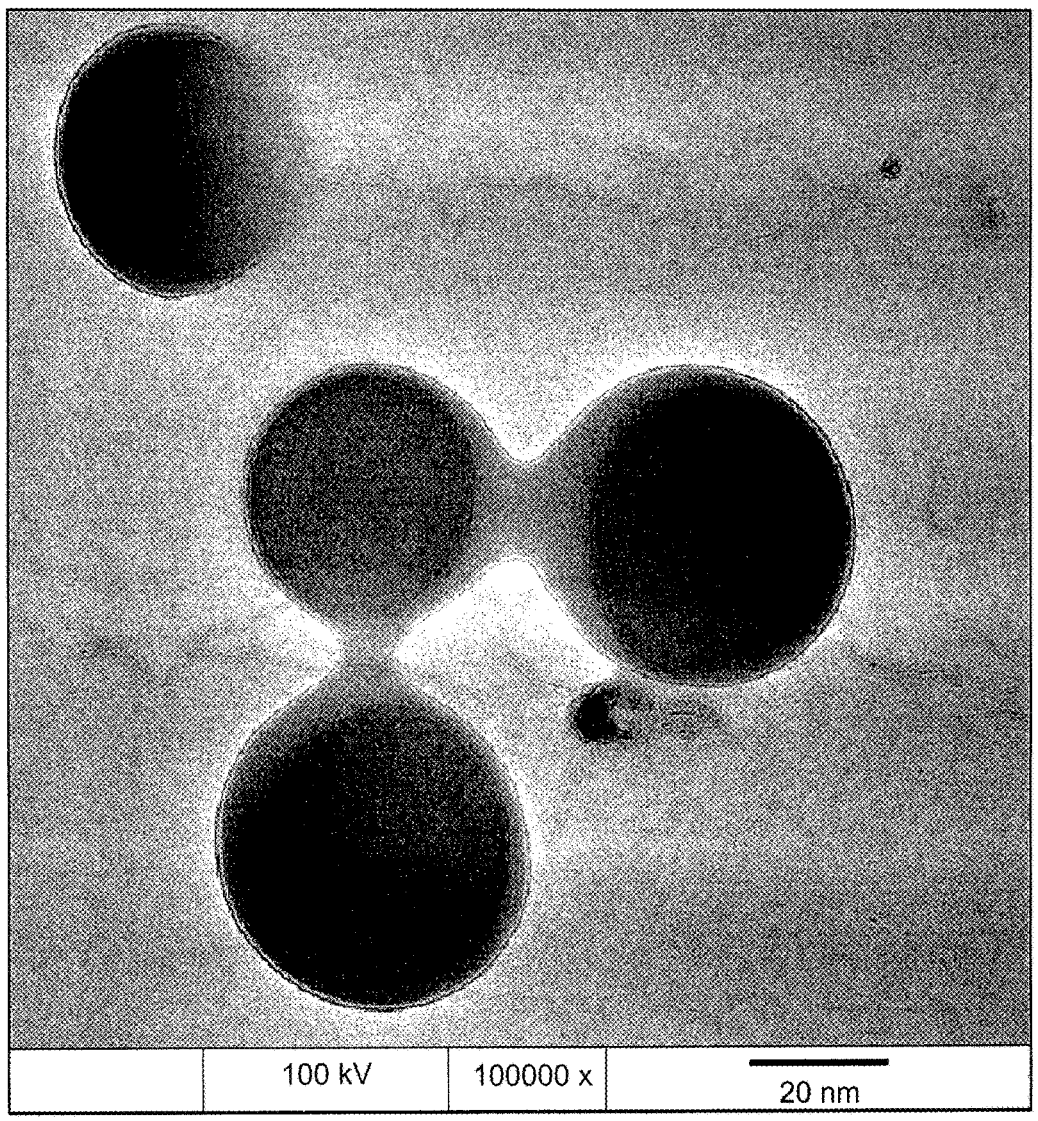
FIG. 2A shows a transmission electron microscopy (TEM) image of the synthesized 3-oxolupenal nanoparticles at 100 kV, at a magnification of 100,00×.
Figure 2B:
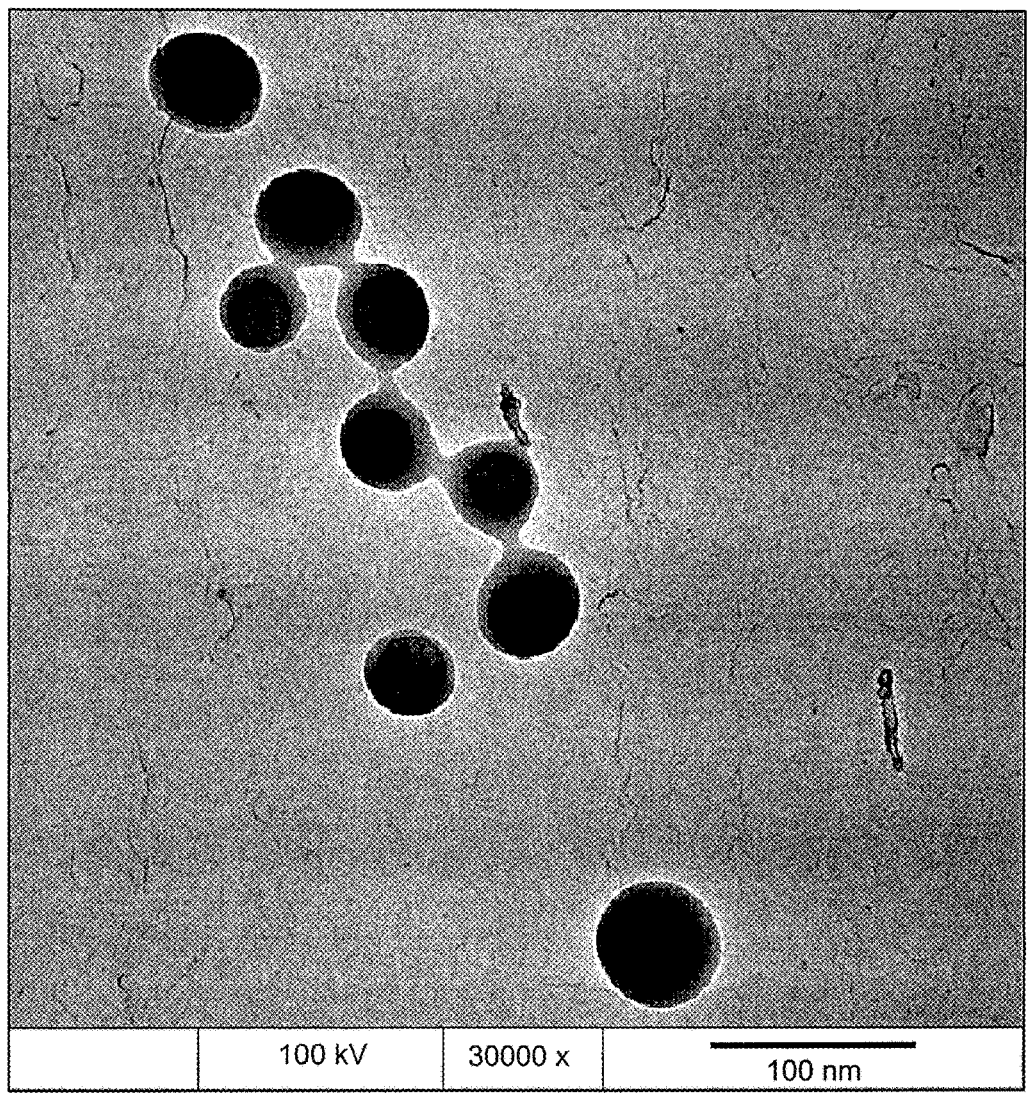
FIG. 2B shows a transmission electron microscopy (TEM) image of synthesized 3-oxolupenal nanoparticles at 100 kV, at a magnification of 30,000×.
Figure 2C:
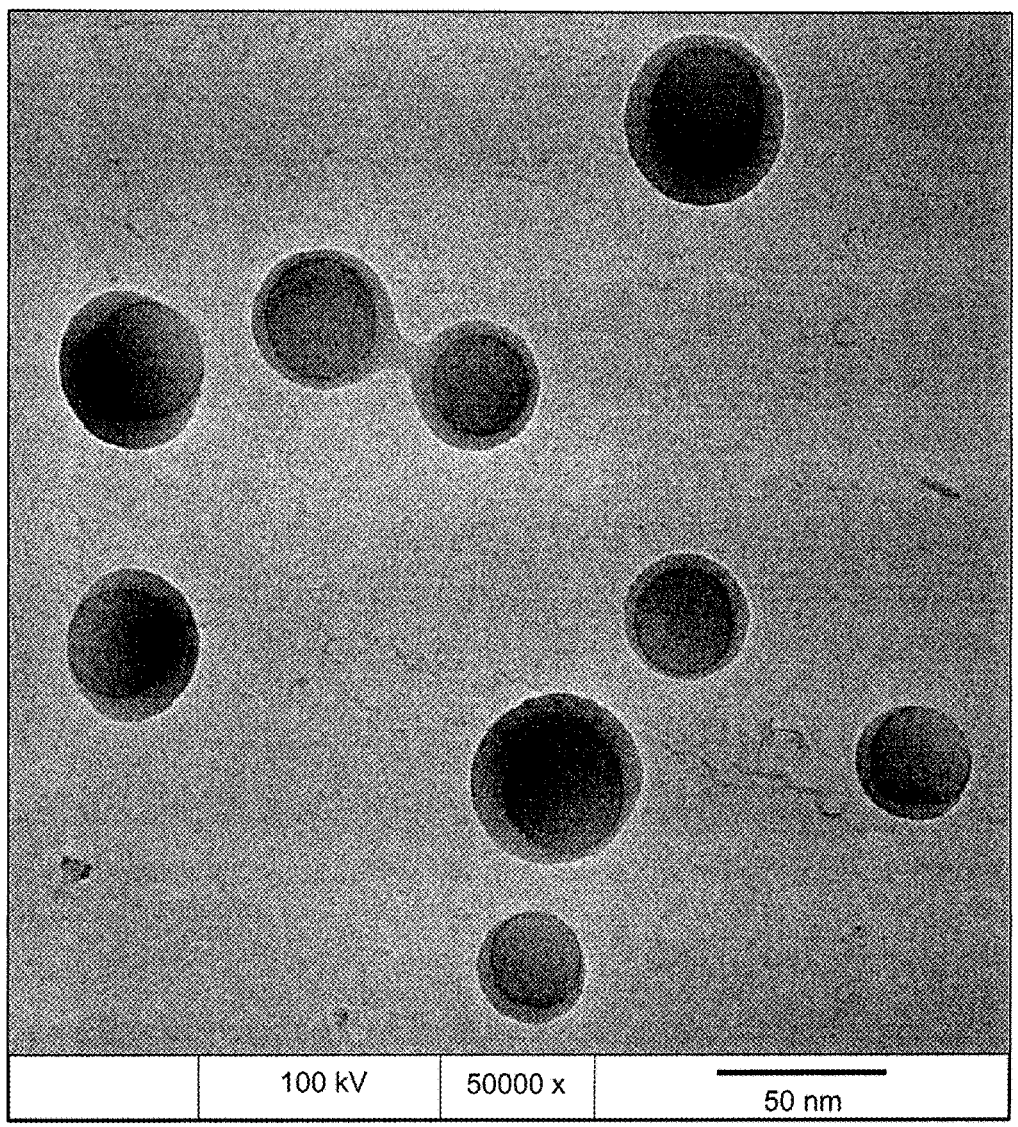
FIG. 2C shows a transmission electron microscopy (TEM) images of synthesized 3-oxolupenal nanoparticles at 100 kV, at a magnification of 50,000×.
Figure 2D:
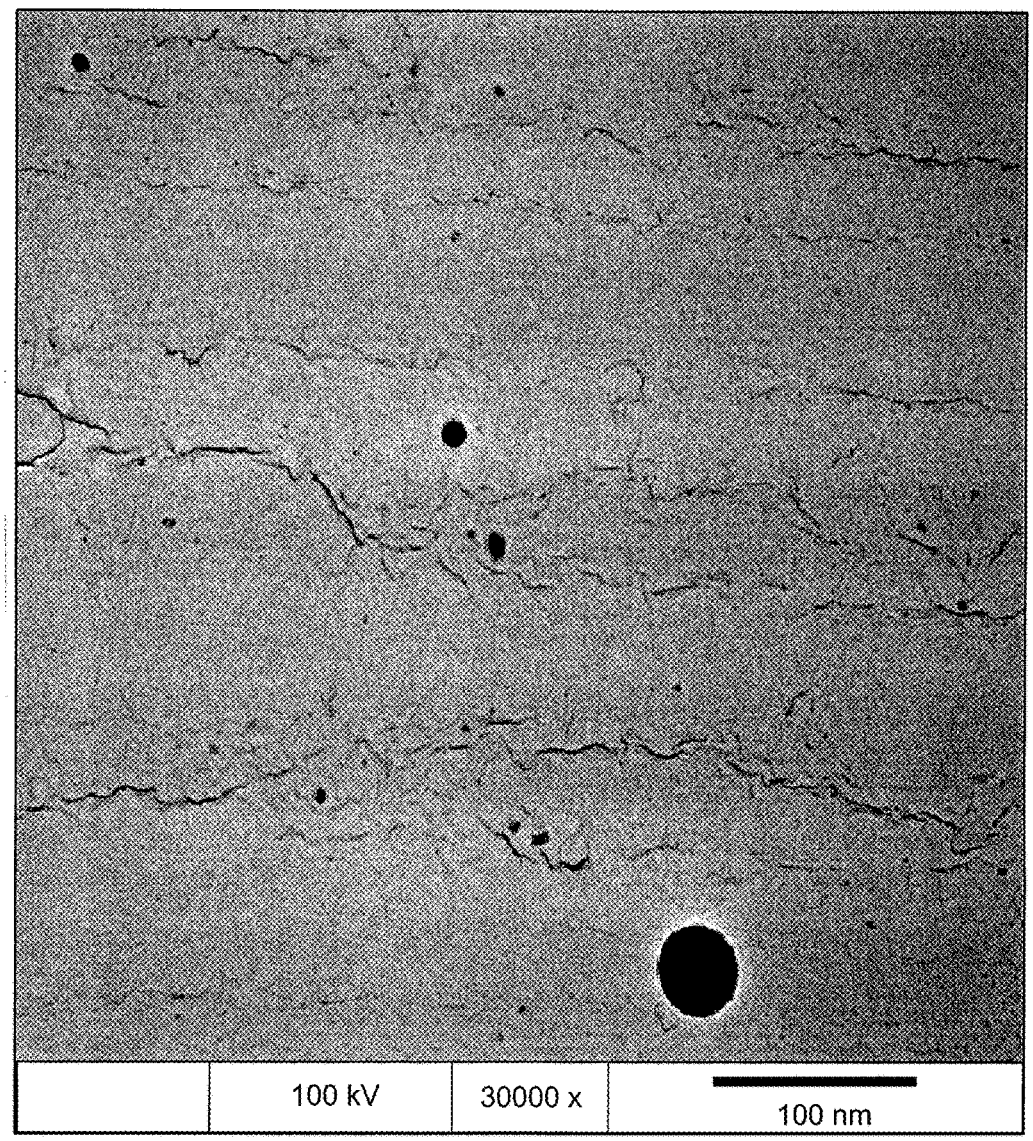
FIG. 2D each show a transmission electron microscopy (TEM) image of synthesized 3-oxolupenal nanoparticles at 100 kV, at a magnification of 30,000×.

Reference will now be made in detail to embodiments of the present disclosure, examples of which are illustrated in the accompanying drawings. For purposes of this disclosure, "nanoparticles" refer to particles having at least one dimension between 1 and 100 nanometers.

Overview

The present method provides a novel synthesis of 3-oxolupenal nanoparticles from the compound 3-oxolup-20(29)-en-30-al. The compound 3-oxolup-20(29)-en-30-al (referred to herein as 3-oxolupenal) can be isolated from *Nuxia oppositifolia*. For example, 3-oxolupenal can be isolated from an n-hexane fraction of the aerial parts of the Saudi plant, *Nuxia oppositifolia* following chromatographic purification techniques. The 3-oxolupenal compound can be reduced to powder form and dissolved in methanol to form a first solution. The first solution can be added to boiling water to form a second solution. The second solution can be sonicated and then freeze-dried to obtain the 3-oxolupenal nanoparticles. The method may further include stirring the second solution after sonication for a predetermined time.

In some embodiments, the first solution may be added dropwise to the boiling water. For example, the first solution can be added to the boiling water using a pipette, or other instrument, one drop at a time. According to an embodiment, the first solution can be added dropwise to boiling water at a predetermined flowrate, such as, e.g., a flowrate of 0.1-03 mL/min. Preferably, the first solution is added to the boiling water under ultrasonic conditions.

The 3-oxolupenal nanoparticles exhibit cytotoxic effects. Specifically, the cytotoxic effect of the synthesized nanoparticles has been evaluated against five cell lines, namely, breast carcinoma cells MCF-7, hepatocellular carcinoma cells HepG-2, human colon carcinoma cells HCT-116, human lung adenocarcinoma epithelial cells A549, and cervical carcinoma cells HeLa. The results of these evaluations are compiled in Tables 1-5 and corresponding FIGS. 3-7.

The 3-oxolupenal nanoparticles can be used as an active ingredient in a composition for inhibiting microbial growth. The microbial growth can include fungal growth and/or bacterial growth. The bacterial growth can include growth of gram positive and/or gram negative bacteria.

The 3-oxolupenal nanoparticles can be used for the treatment of proliferative diseases, such as cancer. For example, the 3-oxolupenal nanoparticles can be included in a pharmaceutical composition for the treatment of cancer, and particularly breast cancer, malignant hepatoma, colon cancer, lung cancer, and/or cervical cancer. The pharmaceutical composition can include a compound of the present invention and a pharmaceutically acceptable carrier, diluent or excipient. The compound can be in an "effective amount" to elicit the biological or medical response of a tissue, system, animal or human that is being sought by the researcher, veterinarian, medical doctor or other clinician. As would be understood by those skilled in the art of treating cancer, the term "treatment" does not necessarily mean that the cancer is completely cured. The term "treatment" encompasses any inhibition of replication of cancer cells and/or reduction in the tumor size in the subject being treated.

The following examples will further illustrate the process of synthesizing 3-oxolupenal nanoparticles.

Compound Isolation and Identification

The compound 3-oxolupenal was isolated from the n-hexane fraction of the aerial parts of the Saudi plant *Nuxia oppositifolia*, following the application of a number of chromatographic purification techniques. The structure was assigned by different spectroscopic methods, including 1 and 2-D NMR and by comparison with published data.

Synthesis of 3-Oxolupenal Nanoparticles

According to one embodiment, about 50 mg of 3-oxolupenal powder was dissolved in 10 mL of methanol to form solution A. Then 5 mL of solution A was added dropwise into 40 mL of boiling water at a flow rate of about 0.1-0.3 mL/min for a period of approximately 10 minutes, under ultrasonic conditions. After sonication for about 20 minutes, the contents were vigorously stirred for about 15 minutes and then freeze-dried to obtain the synthesized 3-oxolupenal nanoparticles.

The synthesized nanoparticles were characterized using Zetasizer, Nano series, HT Laser, ZEN3600 from Molvern Instrument, UK to determine the average size of the resulting nanoparticles. FIG. 1 shows a graph of the average particle size of synthesized 3-oxolupenal nanoparticles. According to the size distribution graph, the average particle size for the synthesized 3-oxolupenal nanoparticles was about 158.3 nanometers. FIGS. 2A-2D show the TEM images of the synthesized 3-oxolupenal nanoparticles at 100 kV at different magnifications. The TEM images were used to characterize the size, shape, and morphologies of the synthesized nanoparticles. The shapes of the nanoparticles typically appear as spherical and elongated spherical shapes. However, the nanoparticle is not limited to spherical shapes and may be provided in various shapes.

Cytotoxicity Evaluation

The 3-oxolupenal nanoparticles exhibited cytotoxic effects. Specifically, the cytotoxic effect of the synthesized nanoparticles was evaluated against five cell lines, namely, breast carcinoma cells (MCF-7), hepatocellular carcinoma cells (HepG-2), human colon carcinoma cells (HCT-116), human lung adenocarcinoma epithelial cells (A549), and cervical carcinoma cells (HeLa). The results of these evaluations are compiled in Tables 1-5 and FIGS. 3-7.

The following examples, with corresponding tables and figures, show the cell viability of three replicates of a cell line (MCF-7, HepG-2, HCT-116, A549, and HeLa) when introduced to a varying concentration of 3-oxolupenal nanoparticles. The mean of the inhibitory activity was taken based on the cell viability of the three replicates and a percent inhibition was determined based on the mean viability of the replicates at each concentration of 3-oxolupenal nanoparticles.

Example 1

Figure 3:
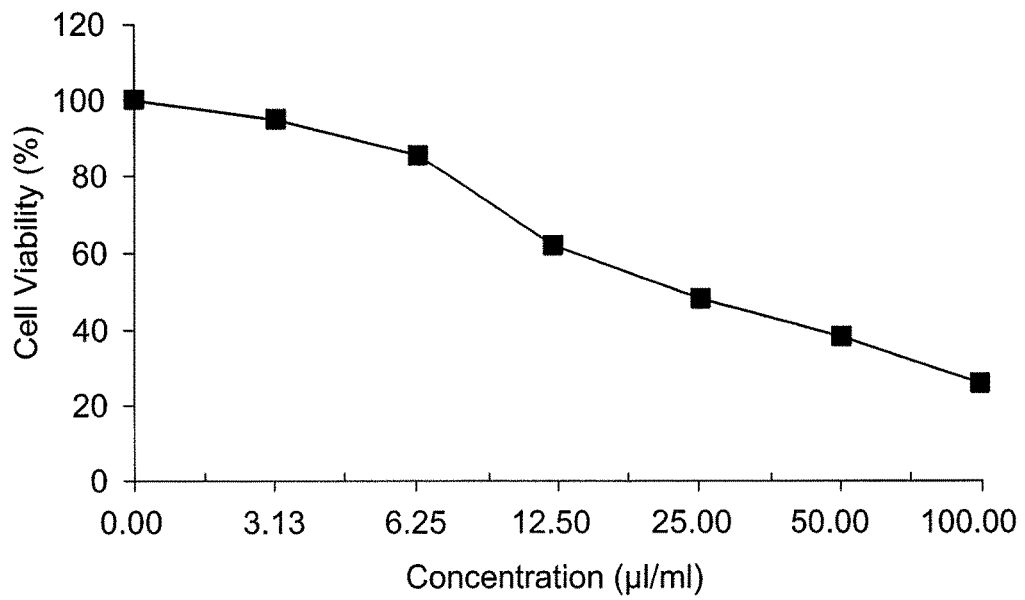
FIG. 3 shows a graph evaluating cytotoxicity of 3-oxolupenal nanoparticles against MCF-7 cell line, at concentrations ranging from 3.13 to 100 µl/ml.

As shown in Table 1 below, the synthesized 3-oxolupenal nanoparticles had an inhibitory effect on the MCF-7 breast carcinoma cells. The $IC_{50}$ dose is calculated to be a concentration of 23.5 μl/mL of 3-oxolupenal nanoparticles. FIG. 3 shows a graph reflecting the cytotoxicity of 3-oxolupenal nanoparticles against MCF-7 cell line, based on the data shown in Table 1. The inhibition of the MCF-7 cell line significantly increased at the higher tested concentrations of 3-oxolupenal nanoparticles. Specifically, the test data indicates 74.16% inhibition of the MCF-7 cell line at a 100 μl/mL concentration of 3-oxolupenal nanoparticles, compared to 4.79% inhibition of the MCF-7 cell line at a 3.125 μl/mL concentration of 3-oxolupenal nanoparticles.

TABLE 1

Inhibitory activity of 3-oxolupenal nanoparticles against MCF-7 cells with $IC_{50}$ = 23.5 μl/mL

| Sample conc. | % Viability (3 Replicates) | | | | % | Standard |
|---|---|---|---|---|---|---|
| (μl/mL) | $1^{st}$ | $2^{nd}$ | $3^{rd}$ | Mean | Inhibition | Deviation (±) |
| 100 | 29.12 | 23.08 | 25.33 | 25.84 | 74.16 | 3.05 |
| 50 | 40.87 | 36.95 | 37.54 | 38.45 | 61.55 | 2.11 |
| 25 | 47.06 | 51.22 | 46.89 | 48.39 | 51.61 | 2.45 |
| 12.5 | 65.78 | 60.94 | 58.71 | 61.81 | 38.19 | 3.61 |
| 6.25 | 89.23 | 85.16 | 82.56 | 85.65 | 14.35 | 3.36 |
| 3.125 | 96.54 | 95.87 | 93.21 | 95.21 | 4.79 | 1.76 |

Example 2

Figure 4:
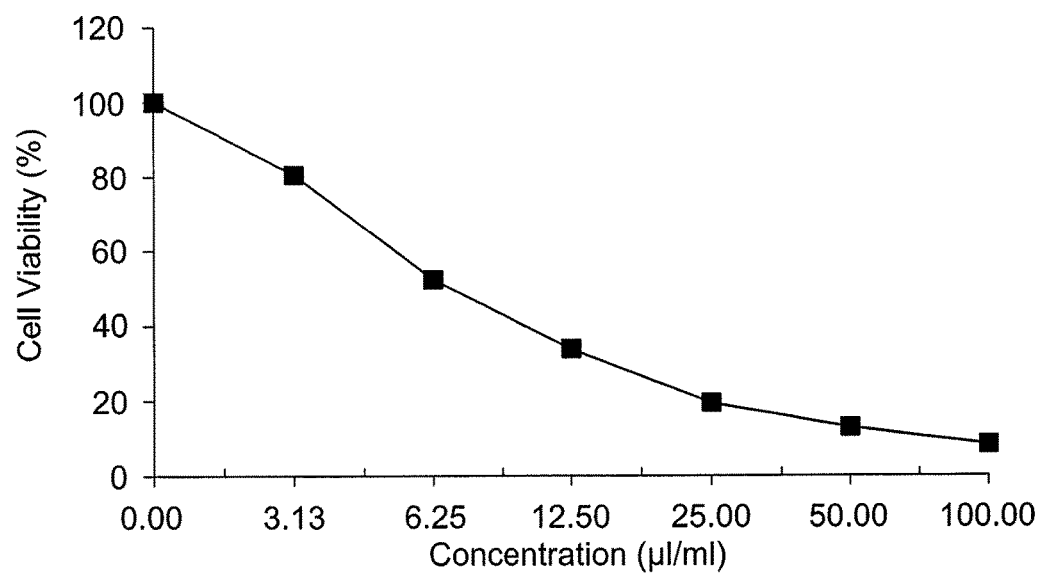
FIG. 4 shows a graph evaluating cytotoxicity of 3-oxolupenal nanoparticles against HepG-2 cell line, at concentrations ranging from 3.13 to 100 µl/ml.

The synthesized 3-oxolupenal nanoparticles demonstrated an inhibitory effect on the hepatocellular carcinoma cells. FIG. 4 shows a graph reflecting cytotoxicity of 3-oxolupenal nanoparticles against HepG-2 cell line, based on the data shown in Table 2. The $IC_{50}$ dose for HepG-2 cells is calculated to be a 3-oxolupenal nanoparticle concentration of 7.01 μl/mL. The inhibition of the HepG-2 cell line samples significantly increased at higher tested concentrations of 3-oxolupenal nanoparticles. Specifically, the test data indicates that there was 91.73% inhibition of the HepG-2 cell line at a concentration of 3-oxolupenal nanoparticles of 100 µl/mL, compared to 19.49% inhibition of the HepG-2 cell line at a concentration of 3-oxolupenal nanoparticles of 3.125 µl/mL.

TABLE 2

Inhibitory activity of 3-oxolupenal nanoparticles against HepG-2 cells with $IC_{50}$ = 7.01 µl/mL.

| Sample conc. | % Viability (3 Replicates) | | | | % | Standard |
|---|---|---|---|---|---|---|
| (µl/mL) | $1^{st}$ | $2^{nd}$ | $3^{rd}$ | Mean | Inhibition | Deviation (±) |
| 100 | 8.34 | 9.59 | 6.87 | 8.27 | 91.73 | 1.36 |
| 50 | 12.97 | 14.25 | 11.32 | 12.85 | 87.15 | 1.47 |
| 25 | 18.24 | 19.72 | 20.48 | 19.48 | 80.52 | 1.14 |
| 12.5 | 34.82 | 30.51 | 36.29 | 33.87 | 66.13 | 3.00 |
| 6.25 | 48.06 | 53.94 | 54.65 | 52.22 | 47.78 | 3.62 |
| 3.125 | 76.91 | 81.37 | 83.24 | 80.51 | 19.49 | 3.25 |

Example 3

Figure 5:
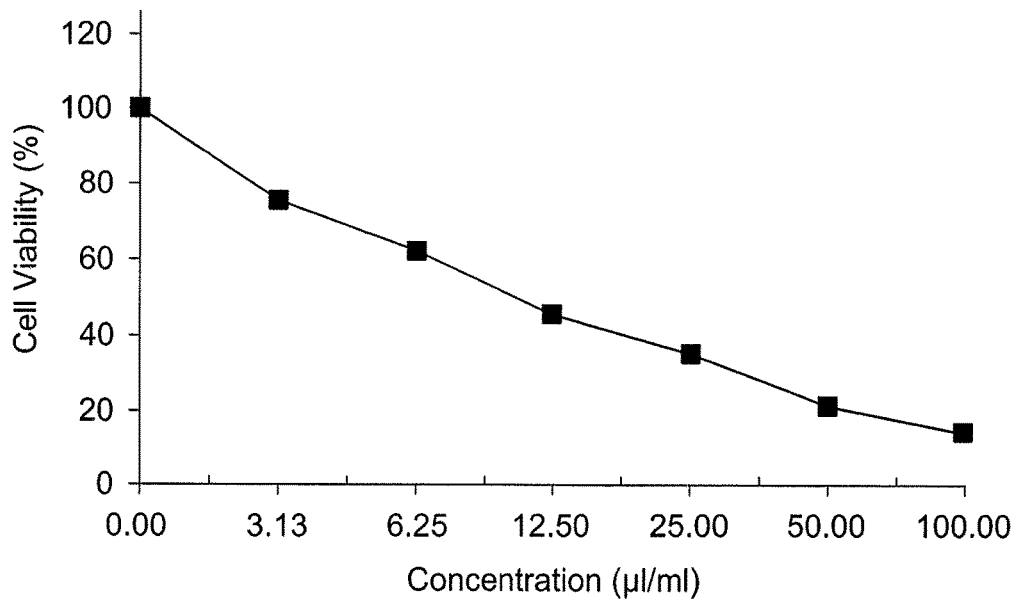
FIG. 5 shows a graph evaluating cytotoxicity of 3-oxolupenal nanoparticles against HCT-116 cell line, at concentrations ranging from 3.13 to 100 µl/ml.

The synthesized 3-oxolupenal nanoparticles demonstrated an inhibitory effect on human colon carcinoma cells. FIG. 5 shows a graph reflecting cytotoxicity of 3-oxolupenal nanoparticles against HCT-116 cell line, based on the data shown in Table 3. The $IC_{50}$ dose for the HCT-116 cells is calculated to be a 3-oxolupenal nanoparticle concentration of 11 µl/mL. The inhibition of the HCT-116 cell line samples significantly increased at higher test concentrations of 3-oxolupenal nanoparticles. Specifically, the test data indicates that there was 85.57% inhibition of the HCT-116 cell line at a concentration of 3-oxolupenal nanoparticles of 100 µl/mL, compared to 24.63% inhibition of the HCT-116 cell line at a concentration of 3-oxolupenal nanoparticles of 3.125 µl/mL.

TABLE 3

Inhibitory activity of 3-oxolupenal nanoparticles against HCT-116 cells with $IC_{50}$ = 11 µl/ml.

| Sample conc. | % Viability (3 Replicates) | | | | % | Standard |
|---|---|---|---|---|---|---|
| (µl/mL) | $1^{st}$ | $2^{nd}$ | $3^{rd}$ | Mean | Inhibition | Deviation (±) |
| 100 | 13.95 | 16.48 | 12.86 | 14.43 | 85.57 | 1.86 |
| 50 | 21.37 | 25.24 | 18.72 | 21.78 | 78.22 | 3.28 |
| 25 | 35.29 | 37.15 | 33.81 | 35.42 | 64.58 | 1.67 |
| 12.5 | 42.86 | 46.93 | 48.02 | 45.94 | 54.06 | 2.72 |
| 6.25 | 61.48 | 60.87 | 64.95 | 62.43 | 37.57 | 2.20 |
| 3.125 | 78.14 | 73.29 | 74.68 | 75.37 | 24.63 | 2.50 |

Example 4

Figure 6:
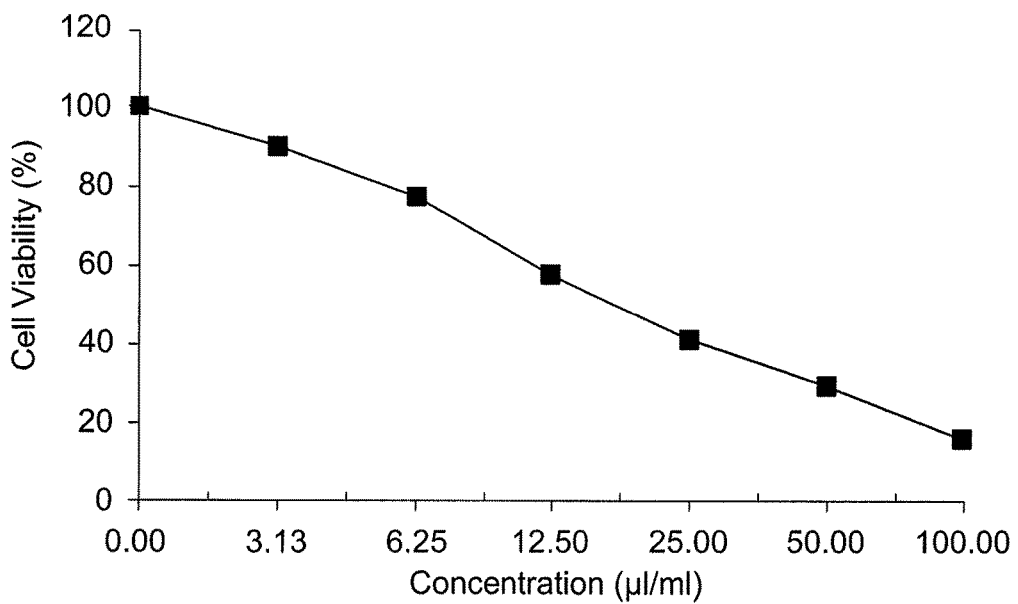
FIG. 6 shows a graph evaluating cytotoxicity of 3-oxolupenal nanoparticles against A-549 cell line, at concentrations ranging from 3.13 to 100 µl/ml.

The synthesized 3-oxolupenal nanoparticles also exhibited an inhibitory effect on human lung adenocarcinoma. FIG. 6 shows a graph reflecting cytotoxicity of 3-oxolupenal nanoparticles against A5492 cell line, based on the data shown in Table 4. The $IC_{50}$ dose for the A549 cells is calculated to be a 3-oxolupenal nanoparticle concentration of 18.4 µl/mL. The inhibition of the A549 cell line samples significantly increased at higher test concentrations of 3-oxolupenal nanoparticles. Specifically, the test data demonstrated an 83.63% inhibition of the A549 cell line at a concentration of 3-oxolupenal nanoparticles of 100 µl/mL, compared to 9.38% inhibition of the A549 cell line at a concentration of 3-oxolupenal nanoparticles of 3.125 µl/mL.

TABLE 4

Inhibitory activity of 3-oxolupenal nanoparticles against A-549 cells with $IC_{50}$ = 18.4 µl/mL.

| Sample conc. | % Viability (3 Replicates) | | | | % | Standard |
|---|---|---|---|---|---|---|
| (µl/mL) | $1^{st}$ | $2^{nd}$ | $3^{rd}$ | Mean | Inhibition | Deviation (±) |
| 100 | 16.87 | 14.93 | 17.32 | 16.37 | 83.63 | 1.27 |
| 50 | 31.49 | 27.65 | 28.91 | 29.35 | 70.65 | 1.96 |
| 25 | 43.21 | 39.46 | 40.67 | 41.11 | 58.89 | 1.91 |
| 12.5 | 57.62 | 53.78 | 62.39 | 57.93 | 42.07 | 4.31 |
| 6.25 | 76.34 | 75.23 | 81.48 | 77.68 | 22.32 | 3.33 |
| 3.125 | 87.08 | 94.12 | 90.65 | 90.62 | 9.38 | 3.52 |

Example 5

Figure 7:
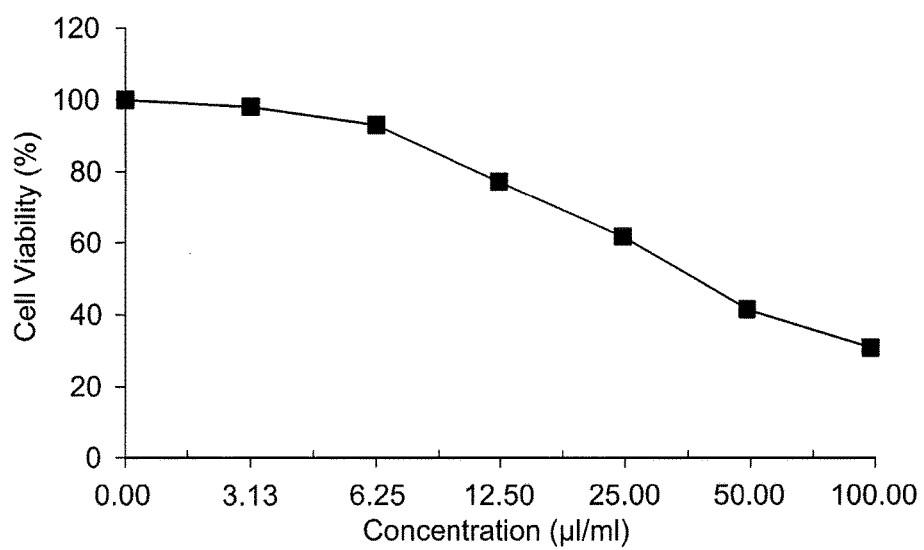
FIG. 7 shows a graph evaluating cytotoxicity of 3-oxolupenal nanoparticles against HeLa cell line, at concentrations ranging from 3.13 to 100 µl/ml.

The 3-oxolupenal nanoparticles demonstrated an inhibitory effect on cervical carcinoma cells. FIG. 7 shows a graph reflecting cytotoxicity of 3-oxolupenal nanoparticles against HeLa cell line based on the data shown in Table 5. The IC50 dose for the HeLa cells is a concentration of 3-oxolupenal nanoparticles of 39.9 µl/mL. Inhibition of the HeLa cell line samples significantly increased at the higher test concentrations of 3-oxolupenal nanoparticles. Specifically, the test data indicates a 68.79% inhibition of the HeLa cell line at a concentration of 3-oxolupenal nanoparticles of 100 µl/mL, compared to 1.03% inhibition of the HeLa cell line at a concentration of 3-oxolupenal nanoparticles of 3.125 µl/mL.

TABLE 5

Inhibitory activity of 3-oxolupenal nanoparticles against HeLa cells with IC50 = 39.9 µl/mL.

| Sample conc. | % Viability (3 Replicates) | | | | % | Standard |
|---|---|---|---|---|---|---|
| (µl/mL) | $1^{st}$ | $2^{nd}$ | $3^{rd}$ | Mean | Inhibition | Deviation (±) |
| 100 | 34.06 | 30.83 | 28.75 | 31.21 | 68.79 | 2.68 |
| 50 | 41.89 | 43.59 | 39.68 | 41.72 | 58.28 | 1.96 |
| 25 | 57.18 | 64.06 | 65.49 | 62.24 | 37.76 | 4.44 |
| 12.5 | 74.21 | 79.47 | 80.23 | 77.97 | 22.03 | 3.28 |
| 6.25 | 94.85 | 96.28 | 89.41 | 93.51 | 6.49 | 3.62 |
| 3.125 | 98.12 | 100 | 98.78 | 98.97 | 1.03 | 0.95 |

Example 6

The synthesized 3-oxolupenal nanoparticles also exhibited antimicrobial activity. Table 6 shows the antimicrobial activity of 3-oxolupenal nanoparticles using agar diffusion technique, for various fungi and bacteria, and compared to reference drugs.

TABLE 6

| | Sample | |
|---|---|---|
| Tested microorganisms | Zone of Inhibition (±S.D.) | Reference drug |
| Fungi | | Amphotericin B |
| *Absidia corymbifera* (RCMB 02564) | 20 ± 0.34 | 23.0 ± 0.10 |
| *Geotricum candidum* (RCMB 05097) | 20 ± 0.73 | 27.0 ± 0.20 |
| *Candida albicans* (RCMB 05036) | 20 ± 0.54 | 25.7 ± 0.10 |
| Gram Positive Bacteria | | Ampicillin |
| *Staphylococcus aureus* | 22 ± 0.23 | 27.3 ± 0.14 |

TABLE 6-continued

| Tested microorganisms | Sample Zone of Inhibition (±S.D.) | Reference drug |
|---|---|---|
| (RCMB 010027) | | |
| *Staphylococcus epidermidis* (RCMB 010024) | 26 ± 0.11 | 25.0 ± 0.18 |
| *Streptococcus pyogenes* (RCMB 010015) | 23 ± 0.68 | 26.3 ± 0.34 |
| Gram Negative Bacteria | | Gentamycin |
| *Proteous vulgaris* (RCMB 010085) | 23 ± 0.75 | 23.4 ± 0.30 |
| *Klebsiella pneumoniae* (RCMB 0010093) | 20.3 ± 0.21 | 26.4 ± 0.15 |
| *Salmonella enteritidis* (RCMB 010084) | 24.3 ± 0.44 | 25.2 ± 0.18 |

It is to be understood that the present subject matter is not limited to the embodiments described above, but encompasses any and all embodiments within the scope of the following claims.

We claim:

1. A method of synthesizing 3-oxolupenal nanoparticles, comprising:
    isolating 3-oxolupenal from an n-hexane fraction of the aerial parts of a fraction of *Nuxia oppositifolia* to obtain isolated 3-oxolupenal;
    reducing the isolated 3-oxolupenal to form a powder of 3-oxolupenal;
    dissolving the powder of 3-oxolupenal in methanol to form a first solution;
    adding the first solution to boiling water to form a second solution;
    sonicating the second solution for 20 minutes;
    stirring the sonicated second solution for 15 minutes; and
    freeze-drying the second solution to obtain the 3-oxolupenal nanoparticles.

2. The method of claim 1, wherein the first solution is added dropwise to the boiling water.

3. The method of claim 2, wherein the first solution is added to the boiling water under ultrasonic conditions.

4. The method of claim 2, wherein the first solution is added to the boiling water at a flow rate of 0.1-0.3 mL/min.

\* \* \* \* \*